(12) United States Patent
Basu et al.

(10) Patent No.: US 10,076,294 B2
(45) Date of Patent: Sep. 18, 2018

(54) GANTRY SYSTEM WITH SUPPORT WHEELS

(71) Applicant: Morpho Detection, LLC, Newark, CA (US)

(72) Inventors: Samit Kumar Basu, Fremont, CA (US); Anthony James Murch, Hayward, CA (US); Jared William Moore, Oakland, CA (US); Pedro Andres Garzon, Santa Clara, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 227 days.

(21) Appl. No.: 15/084,700

(22) Filed: Mar. 30, 2016

(65) Prior Publication Data

US 2017/0281105 A1 Oct. 5, 2017

(51) Int. Cl.
*A61B 6/03* (2006.01)
*A61B 6/00* (2006.01)
*F16C 19/50* (2006.01)

(52) U.S. Cl.
CPC ............ *A61B 6/4435* (2013.01); *A61B 6/035* (2013.01); *F16C 19/507* (2013.01)

(58) Field of Classification Search
CPC ....... A61B 6/465; A61B 8/4209; A61B 6/461; A61B 5/0077; A61B 8/4427
See application file for complete search history.

(56) References Cited

U.S. PATENT DOCUMENTS

| 3,836,103 A | 9/1974 | Retali et al. |
| 5,044,789 A | 9/1991 | Damon et al. |
| 5,784,428 A | 7/1998 | Schmidt |
| 2002/0168044 A1* | 11/2002 | Tybinkowski ....... A61B 6/4447 378/4 |
| 2012/0148013 A1 | 6/2012 | Zhang et al. |

(Continued)

FOREIGN PATENT DOCUMENTS

DE 102013227060 A1 6/2015

OTHER PUBLICATIONS

European Search Report, Application No. 17000423.8, dated Aug. 22, 2017, 7 pps.

(Continued)

*Primary Examiner* — Don Wong
(74) *Attorney, Agent, or Firm* — Armstrong Teasdale LLP

(57) ABSTRACT

A computed tomography (CT) gantry system is described herein. The CT gantry system includes a frame, a plurality of support wheels rotatably coupled to the frame, and a gantry resting upon the plurality of support wheels. In some embodiments, the gantry includes two gantry rings, and a cross member extending between the two gantry rings. In other embodiments, the gantry includes a first gantry ring, and a second gantry ring spaced apart from the first gantry ring in a direction parallel to an axis of rotation of the gantry. In some embodiments, the plurality of support wheels includes a plurality of front support wheels and a plurality of back support wheels. In some embodiments, the gantry includes a front gantry ring resting upon the front support wheels, a back gantry ring resting upon the back support wheels, and a cross member coupled between the front and back gantry rings.

20 Claims, 3 Drawing Sheets

(56) References Cited

U.S. PATENT DOCUMENTS

2013/0077737 A1    3/2013    Fasoli
2014/0119515 A1    5/2014    McKenna
2015/0030136 A1*  1/2015    Dodge .................... H05G 1/02
                                                        378/204

OTHER PUBLICATIONS

Microtec: CT Log, retrieved from: http://microtec.eu/en/catalogue/products/ctlog/ , accessed Mar. 30, 2016.

* cited by examiner

GANTRY SYSTEM WITH SUPPORT WHEELS

BACKGROUND

The embodiments described herein relate generally to gantry systems, and more particularly, to gantry systems including a two-ring gantry rotatably supported by a plurality of support wheels.

Computed tomography (CT) imaging systems typically include a rotatable gantry configured to capture images of object(s) channeled therethrough. In at least some known CT systems, the gantries are rotatably supported within a frame by one or more slew bearings. The slew bearing is commonly installed on one side (e.g., a front side or a back side) of the gantry, such that the gantry is cantilevered off of the bearing. This cantilever support increases a required stiffness of a bearing interface of the slew bearing and increases a complexity of the gantry system. In particular, replacement, repair, and serviceability of these gantry systems, particularly the slew bearings, may be very difficult. Moreover, the use of slew bearings may impose an upper limit on the rotational speed of the gantry, as slew bearings are suited for low-speed applications.

One attempt to overcome these difficulties includes the development and installation of customized slew bearings for a particular gantry system. However, the cost of customized bearings is high, and customized bearings often require additional and/or specialized maintenance thereof.

BRIEF SUMMARY

In one aspect, a computed tomography (CT) gantry system is provided. The CT gantry system includes a frame, a plurality of support wheels rotatably coupled to the frame, and a gantry resting upon the plurality of support wheels. The gantry includes two gantry rings, and at least one cross member extending between the two gantry rings.

In another aspect, a computed tomography (CT) gantry system is provided. The CT gantry system includes a frame, a plurality of support wheels rotatably coupled to the frame, and a gantry resting upon the plurality of support wheels. The gantry includes a first gantry ring, and a second gantry ring spaced apart from the first gantry ring in a direction parallel to an axis of rotation of the gantry.

In yet another aspect, a computed tomography (CT) gantry system is provided, the CT gantry system including a frame, a plurality of support wheels rotatably coupled to the frame, and a gantry. The plurality of support wheels includes a plurality of front support wheels, and a plurality of back support wheels. The gantry includes a front gantry ring resting upon the plurality of front support wheels, a back gantry ring resting upon the plurality of back support wheels, and at least one cross member coupled between the front gantry ring and the back gantry ring.

DETAILED DESCRIPTION

The gantry system described herein includes a gantry and a plurality of support wheels that rotatably support the gantry. More specifically, in one embodiment, the gantry includes two gantry rings, and each of the two gantry rings rests upon at least one of the plurality of support wheels. Each of the plurality of support wheels is coupled to one of the two gantry rings at a rotatable contact point, such that the gantry rotates with rotation of the support wheels. In the example embodiment, the plurality of support wheels are evenly divided between the two gantry rings, such that the support wheels provide balanced support for the gantry. A gantry that is supported on both sides (and as such does not impose a cantilever on a bearing, as in other gantry systems) has lower requirements on a rigidity of gantry and support wheels surfaces. Moreover, as the gantry is coupled to the support rings by resting the gantry upon the support wheels, the gantry system is easily serviced by lifting the gantry upwards and off of the support wheels. In addition, the support wheels are capable of driving high speed gantry rotation. In some embodiments, the support wheels enable gantry rotation of at least about 150 RPM, or at least about 200 RPM, or at least about 250 RPM, or greater rotational speeds. Higher speed gantry rotation enables faster and/or increased throughput of the gantry system. Accordingly, the gantry system described herein provides rotatable, balanced support for high rotational speed applications and with improved serviceability to overcome the above-described issues.

As used herein, the terms "large diameter" and "small diameter" are relative terms in that "small diameter" refers to diameters smaller than any "large diameter." In one example embodiment, although not meant to limit the scope of the present disclosure, a "large-diameter gantry" may refer to a gantry having a diameter from about 0.25 m to 50 m, or from about 0.5 m to about 1.5 m, or, more particularly, from about 1.0 m to about 1.2 m. Moreover, in another example embodiment, although not meant to limit the scope of the present disclosure, a "small-diameter support wheel" may refer to a support wheel having a diameter less than about 1.0 m. In one embodiment, the diameter or size of the support wheel is optimized to minimize linear speed and temperature thereof while maintaining structural strength of the gantry system.

Figure 1:
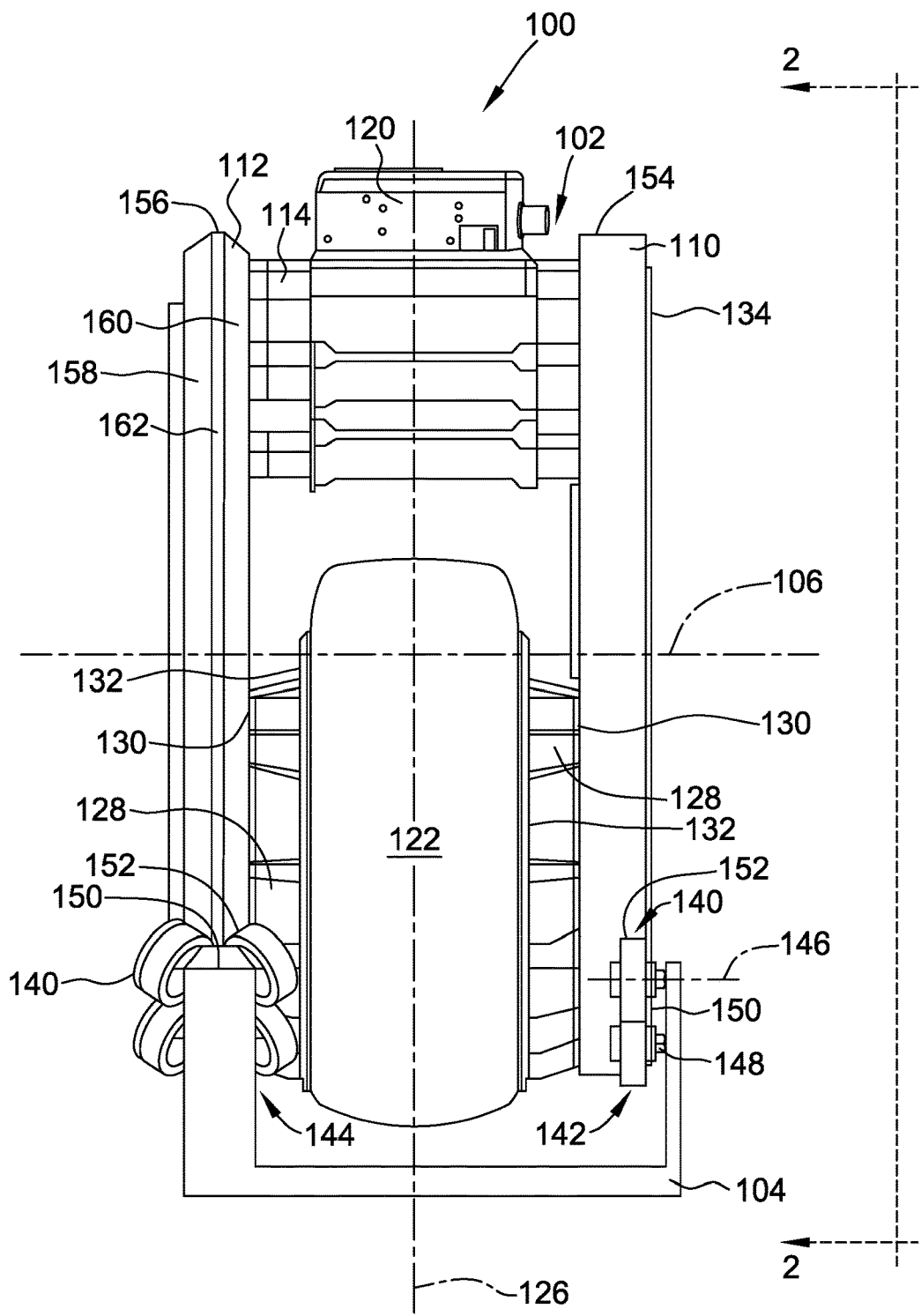
FIG. 1 is a side view of one example embodiment of a gantry system in accordance with the present disclosure.
Figure 2:
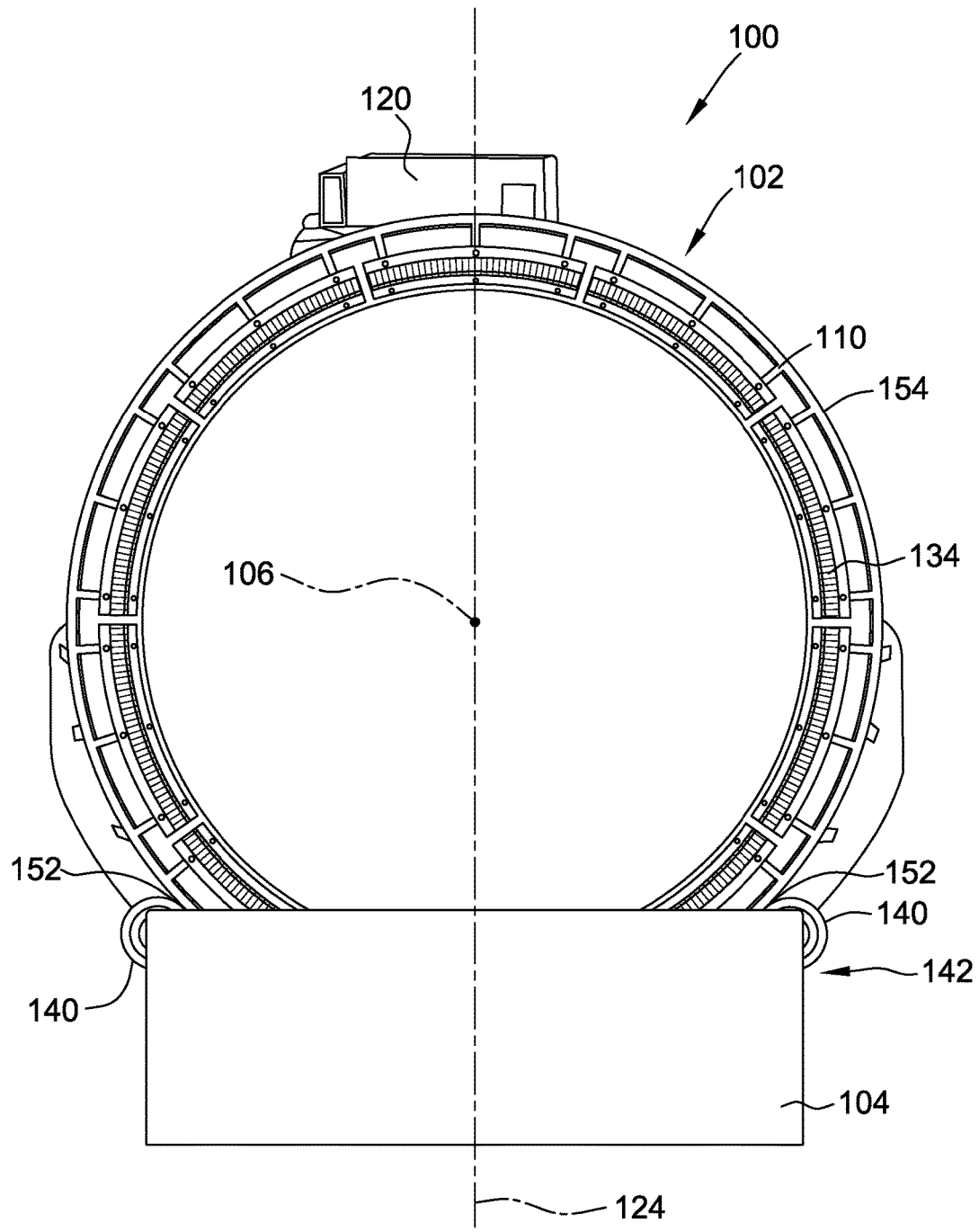
FIG. 2 is a front view of the gantry system shown in FIG. 1.
Figure 3:
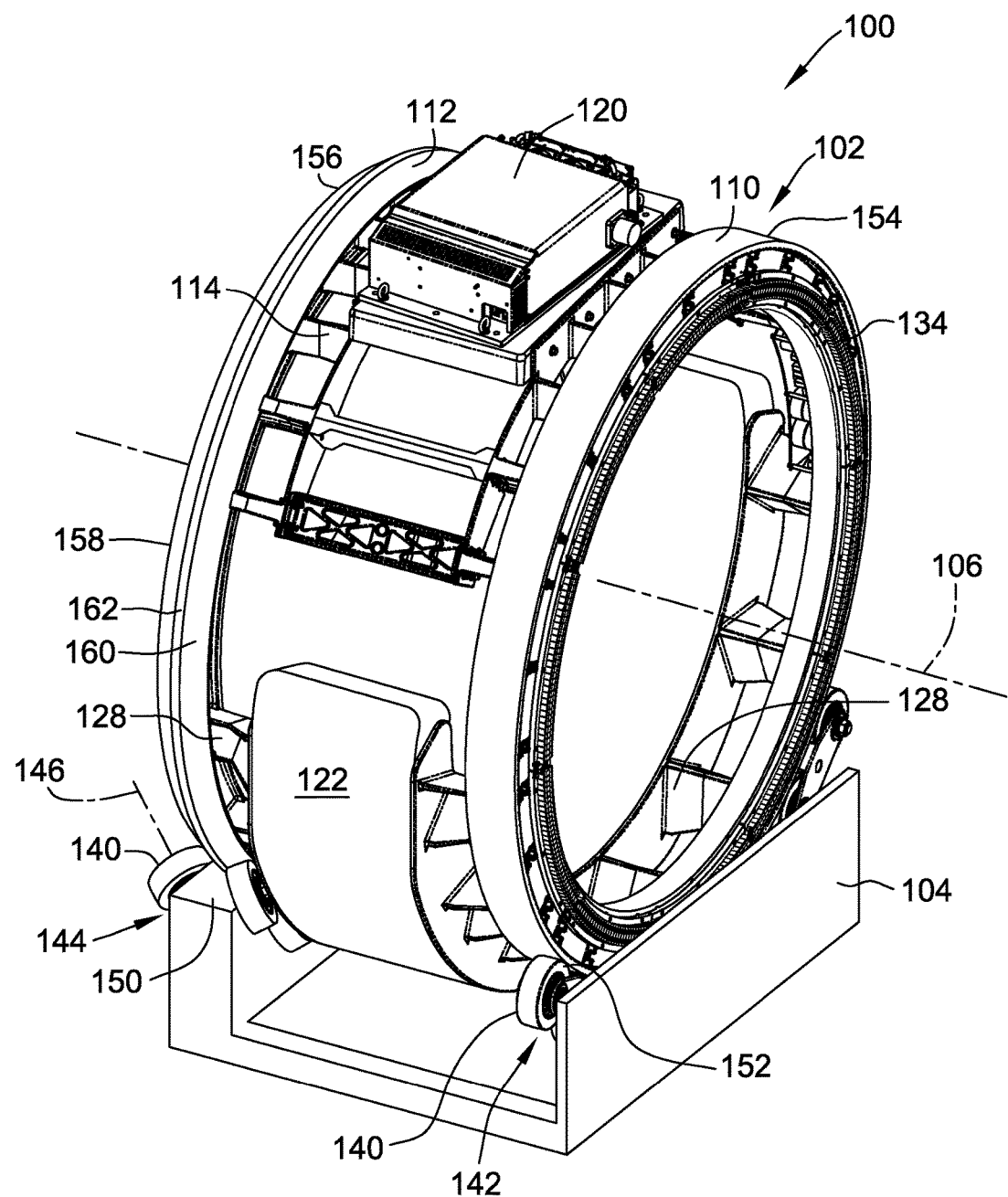
FIG. 3 is a perspective view of the gantry system shown in FIG. 1.

Turning now to the figures, FIGS. 1-3 illustrate one example embodiment of a gantry system 100 in accordance with the present disclosure. More specifically, FIG. 1 is a side view of gantry system 100, FIG. 2 is a front view of gantry system 100 (taken along the line 2-2 shown in FIG. 1), and FIG. 3 is a perspective view of gantry system 100. Gantry system 100 includes a large-diameter gantry 102 that is rotatable with respect to a frame 104 about an axis of rotation 106. Gantry 102 includes two gantry rings 110, 112 spaced apart from one another in a direction parallel to axis of rotation 106. Gantry ring 110 may be referred to herein as a "first" or "front" gantry ring 110. Gantry ring 112 may be referred to herein as a "second" or "back" gantry ring 112. At least one cross member 114 extends between first gantry ring 110 and second gantry ring 112. The at least one cross member 114 is coupled to both gantry rings 110, 112 and provides structural support to gantry 102, preventing movement of gantry rings 110, 112 relative to one another. In one embodiment, gantry rings 110, 112 and cross member(s) 114 are fabricated from steel. In other embodiments, gantry rings 110, 112 and/or cross member(s) 114 may be fabricated from any suitable material, such as an aluminum alloy, cast iron, a composite material, and/or a combination thereof. Gantry 102 may include additional material spanning between gantry rings 110, 112. Alternatively, gantry 102 may be substantially "open" between gantry rings 110 and 112, as shown.

Gantry 102 further includes at least one x-ray generator 120 and at least one detector 122. In some embodiments, x-ray generator 120 is coupled to and/or supported by one or more cross members 114. In other embodiments, x-ray generator 120 is otherwise coupled to at least one of gantry rings 110, 112. In the example embodiment, x-ray generator 120 is coupled to gantry rings 110, 112 and/or cross member(s) 114 in a weight-balanced configuration or position. "Weight-balanced" or "balanced" may refer to "left-to-right" balance with respect to a first axis 124 and/or may refer to "front-to-back" balance with respect to a second axis 126. Similarly, in some embodiments, detector 122 is coupled to and/or supported by one or more cross members 114. In other embodiments, detector 122 is otherwise coupled to at least one of gantry rings 110, 112. For example, detector 122 may be coupled to gantry rings 110, 112 using one or more partial cross member(s) 128. Each partial cross member 128 extends from and/or is coupled to one of gantry rings 110, 112 at an external end 130 of the partial cross member 128. At an opposing internal end 132 of partial cross member 128, partial cross member 128 is coupled to detector(s) 122. In the example embodiment, detector 122 is coupled to gantry rings 110, 112 and/or cross member(s) 114 in a weight-balanced configuration or position. X-ray generator 120 is configured to generate x-rays that pass through an object (not shown) being imaged using gantry system 100. The x-rays are then are detected using detector 122 to image the object. The functionality of x-ray generators 120 and detector 122 is well known and, accordingly, will not be discussed in detail herein.

Gantry 102 further includes one or more communication channels 134. In the example embodiment, communication channel(s) 134 are integrally coupled to at least one of gantry rings 110, 112. For example, communication channels 134 may be disposed on, adhered to, and/or otherwise coupled to gantry ring(s) 110, 112. Communication channel(s) 134 may be configured to facilitate electrical communication, such as data and/or power transfer, thereacross. Communication channel(s) 134 may communicate to one or more stationary or rotating contact(s) (not shown) in mechanical and electrical contact therewith. Additionally or alternatively, communication channel(s) 134 may be configured for wireless data transfer to one or more receiver(s) (not shown) outside of gantry system 100. In some embodiments, communication channel(s) 134 may facilitate communication of image data from detector(s) 122 outside of gantry system 100.

Gantry system 100 further includes a plurality of support wheels 140. Support wheels 140 are coupled between frame 104 and gantry 102. In particular, support wheels 140 are arranged beneath gantry 102, such that gantry 102 rests on support wheels 140. In the example embodiment, support wheels 140 are distributed beneath gantry 102 to provide balanced support of gantry 102. For example, as in the illustrated embodiment, support wheels 140 may be evenly distributed with respect to first axis 124. Additionally or alternatively, support wheels 140 may be evenly distributed with respect to second axis 126. Each support wheel 140 rotates about a corresponding axis of rotation 146. In the example embodiment, each axis of rotation 146 corresponds to a physical axis 148, by which the support wheel 140 is coupled to frame 104. Accordingly, support wheels 140 are "rotatably coupled" to frame 104. In some embodiments, each axis 148, in turn, is coupled to a bracket 150. Each bracket 150 is coupled to frame 104.

Support wheels 140 contact gantry rings 110, 112 at a rotatable contact point 152. The term "rotatable" contact point refers generally to a contact point defined between two rotating objects (i.e., gantry rings 110, 112 and support wheels 140, in this example) experiencing static (not kinetic) friction therebetween. Simultaneous rotation of support wheels 140 in a first direction (e.g., clockwise) effects rotation of gantry rings 110, 112 in a second, opposite direction (e.g., counterclockwise) through rotatable contact points 152.

In the example embodiment, support wheels 140 are fabricated from a polymer. Accordingly, a lubricant between support wheels 140 and gantry rings 110, 112 may not be needed. As such, gantry system 100 may require less maintenance and/or service than other CT gantry systems in which a lubricant between a gantry and bearing or support is required. Support wheels 140 may be fabricated from any suitable material for which lubrication is not required, such as polyurethane, any other polymer or composite material, and/or brass. Moreover, support wheels 140 may, in some embodiments, be fabricated from steel and/or cast iron. In such embodiments, gantry rings 110, 112 may be fabricated from a composite (e.g., polymer) material, such that no lubrication is needed. Alternatively, in such embodiments, both support wheels 140 and gantry rings 110, 112 may be fabricated from steel, and lubrication may be used in gantry system 100.

In the particular example of the illustrated embodiment, gantry system 100 includes twelve support wheels 140. Specifically, four "front" support wheels 142 are coupled to frame 104 beneath first gantry ring 110. In other words, first gantry ring 110 rests on four front support wheels 142. Front support wheels 142 are evenly distributed, in two pairs, with respect to axis 124, such that first gantry ring 110 is "left-to-right" balanced. First gantry ring 110 includes a substantially planar outer surface 154. The four front support wheels 142 are coupled flush against outer surface 154.

In addition, eight "back" support wheels 144 are coupled to frame 104 beneath second gantry ring 112. In other words, second gantry ring 112 rests on eight back support wheels 144. Back support wheels 144 are also evenly distributed, in two sets with two pairs in each set, with respect to axis 124, such that second gantry ring 112 is "left-to-right" balanced. Accordingly, the entirety of gantry 102 is "left-to-right" balanced on support wheels 140 with respect to axis 124.

In general, at least one of first and second gantry rings 110, 112 may possess a feature of revolution that prevents substantial motion of gantry 102 in the direction parallel to axis of rotation 106, in forward and/or reverse direction(s). Such features of revolution might include, but are not limited to, chamfers, fillets, a convex parabola or other conic section, or concave parabola or other conic section.

In the illustrated embodiment, the example feature of revolution to prevent substantial motion of gantry 102 parallel to axis of rotation 106 is a "double-chamfered" outer surface 156 of second gantry ring 112. Outer surface 156 has two planar faces 158, 160 extending from a midline 162. Each face 158, 160 may extend at the same angle from midline 162. Alternatively, one of faces 158, 160 may extend from midline 162 at a different angle than the other of faces 158, 160. For example, one of faces 158, 160 may extend from midline 162 at a right angle, such that outer surface 156 is only "single-chamfered" along the other of faces 158, 160. Moreover, midline 162 may represent a linear midline of outer surface 156 that bisects outer surface 156, such that faces 158, 160 have substantially equivalent widths. Alternatively, midline 162 may not bisect outer surface 156, such that one of faces 158, 160 is wider than the other of faces 158, 160. In the illustrated embodiment, the eight back support wheels 144 are coupled flush against outer surface 156. More specifically, the eight back support wheels 144 include four pairs of back support wheels 144, wherein two pairs are coupled flush against face 158 and two pairs are coupled flush against face 160. In the illustrated embodiment, gantry 102 may not be "front-to-back" balanced with respect to axis 126, such that gantry ring 112 needs the additional support provided by a great number of back support wheels 144 than of front support wheels 142. Alternatively, the illustrated configuration of second gantry ring 112 may provide additional support for gantry 102, preventing movement of gantry 102 parallel to axis of rotation 106. In other words, back support wheels 144 may provide a "grip" function on gantry 102.

It should be understood that in alternative embodiments, second gantry ring 112 may have a planar outer surface 156 similar to outer surface 154. In such embodiments, gantry system 100 may include only eight support wheels 140, with only four back support wheels 144 beneath second gantry ring 112. Moreover, it should be understood that first gantry ring 110 may additionally or alternatively have a double-chambered outer surface 154 similar to outer surface 156. Additionally, it should be understood that gantry system 100 may include fewer or more support wheels 140 than illustrated without departing from the scope of the disclosure.

In the illustrated embodiment, gantry 102 is only coupled to frame 104 by resting upon support wheels 140. In other words, there is no additional frame component above gantry 102. Accordingly, gantry system 100 may be serviced by lifting gantry 102 from support wheels 140 (e.g., using a lift or a jack), which provides access to substantially the entirety of gantry system 100.

Exemplary embodiments of methods and systems are described above in detail. The methods and systems are not limited to the specific embodiments described herein, but rather, components of systems and/or steps of the methods may be used independently and separately from other components and/or steps described herein. Accordingly, the exemplary embodiment can be implemented and used in connection with many other applications not specifically described herein. For example, the above-described gantry resting on support wheels may be implemented in any suitable rotating system, including those with large diameter rotor components.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computed tomography (CT) gantry system comprising:
   a frame;
   a plurality of support wheels rotatably coupled to the frame; and
   a gantry resting upon the plurality of support wheels, the gantry comprising:
      two gantry rings; and
      at least one cross member extending between the two gantry rings, wherein at least one of the two gantry rings comprises a double-chamfered outer surface having a first planar face and a second planar face, wherein a first pair of the plurality of support wheels is coupled flush against the first planar face, and wherein a second pair of the plurality of support wheels is coupled flush against the second planar face.

2. The CT gantry system of claim 1, wherein the two gantry rings rest upon the plurality of support wheels.

3. The CT gantry system of claim 1, wherein the plurality of support wheels comprises a plurality of front support wheels and a plurality of back support wheels, and wherein the two gantry rings comprise a front gantry ring resting upon the plurality of front support wheels and a back gantry ring resting upon the plurality of back support wheels.

4. The CT gantry system of claim 1, wherein the gantry is weight balanced upon the plurality of support wheels.

5. The CT gantry system of claim 1 further comprising a communication channel coupled to at least one of the two gantry rings, the communication channel configured to transfer at least one of data and power.

6. The CT gantry system of claim 1, wherein each of the plurality of support wheels is fabricated from a polymer.

7. The CT gantry system of claim 1, wherein at least one of the two gantry rings comprises a planar outer surface.

8. The CT gantry system of claim 1, wherein at least one of the two gantry rings comprises a feature of revolution configured to prevent substantial motion of the gantry in a direction parallel to an axis of rotation of the gantry.

9. The CT gantry system of claim 1 further comprising an x-ray generator coupled to the at least one cross member.

10. The CT gantry system of claim 1 further comprising a detector coupled to the at least one cross member.

11. A computed tomography (CT) gantry system comprising:
   a frame;
   a plurality of support wheels rotatably coupled to the frame; and
   a gantry resting upon the plurality of support wheels, the gantry comprising:
      a first gantry ring; and
      a second gantry ring spaced apart from the first gantry ring in a direction parallel to an axis of rotation of the gantry, wherein at least one of the first gantry ring and the second gantry ring comprises a double-chamfered outer surface having a first planar face and a second planar face, wherein a first pair of the plurality of support wheels is coupled flush against the first planar face, and wherein a second pair of the plurality of support wheels is coupled flush against the second planar face.

12. The CT gantry system of claim 11, wherein the plurality of support wheels comprises a plurality of front support wheels and a plurality of back support wheels, wherein the first gantry ring rests upon the plurality of front support wheels, and wherein the second gantry ring rests upon the plurality of back support wheels.

13. The CT gantry system of claim 11, wherein the gantry is weight balanced upon the plurality of support wheels.

14. The CT gantry system of claim 11 further comprising a communication channel coupled to at least one of the first gantry ring and the second gantry ring, the communication channel configured to transfer at least one of data and power.

15. The CT gantry system of claim 11, wherein each of the plurality of support wheels is fabricated from a polymer.

16. The CT gantry system of claim 11, wherein the first gantry ring comprises a planar outer surface.

17. The CT gantry system of claim 11, wherein at least one of the first gantry ring and the second gantry ring comprises a feature of revolution configured to prevent substantial motion of the gantry in a direction parallel to the axis of rotation.

18. The CT gantry system of claim 11 further comprising an x-ray generator coupled to the gantry between the first gantry ring and the second gantry ring.

19. The CT gantry system of claim 11 further comprising a detector coupled to the gantry between the first gantry ring and the second gantry ring.

20. A computed tomography (CT) gantry system comprising:
   a frame;
   a plurality of support wheels rotatably coupled to the frame, the plurality of support wheels comprising:
      a plurality of front support wheels; and
      a plurality of back support wheels; and
   a gantry comprising:
      a front gantry ring resting upon the plurality of front support wheels;
      a back gantry ring resting upon the plurality of back support wheels, wherein the back gantry ring comprises a double-chamfered outer surface having a first planar face and a second planar face, wherein a first pair of the plurality of back support wheels is coupled flush against the first planar face, and wherein a second pair of the plurality of back support wheels is coupled flush against the second planar face; and
      at least one cross member coupled between the front gantry ring and the back gantry ring.

* * * * *